United States Patent
Park et al.

(10) Patent No.: US 12,023,138 B2
(45) Date of Patent: Jul. 2, 2024

(54) APPARATUS AND METHOD FOR ESTIMATING BIO-INFORMATION

(71) Applicant: SAMSUNG ELECTRONICS CO., LTD., Suwon-si (KR)

(72) Inventors: Sang Yun Park, Hwaseong-si (KR); Chang Mok Choi, Suwon-si (KR); Jae Min Kang, Seoul (KR); Seung Woo Noh, Seongnam-si (KR); Hye Rim Lim, Suwon-si (KR); Jin Woo Choi, Suwon-si (KR)

(73) Assignee: SAMSUNG ELECTRONICS CO., LTD., Suwon-si (KR)

( * ) Notice: Subject to any disclaimer, the term of this patent is extended or adjusted under 35 U.S.C. 154(b) by 466 days.

(21) Appl. No.: 17/149,204

(22) Filed: Jan. 14, 2021

(65) Prior Publication Data
US 2022/0104714 A1 Apr. 7, 2022

(30) Foreign Application Priority Data
Oct. 5, 2020 (KR) .................. 10-2020-0127934

(51) Int. Cl.
*A61B 5/021* (2006.01)
*A61B 5/02* (2006.01)
(Continued)

(52) U.S. Cl.
CPC ...... *A61B 5/02108* (2013.01); *A61B 5/02007* (2013.01); *A61B 5/02225* (2013.01); *A61B 5/02427* (2013.01); *A61B 2562/0247* (2013.01)

(58) Field of Classification Search
None
See application file for complete search history.

(56) References Cited

U.S. PATENT DOCUMENTS 6,714,804 B2 * 3/2004 Al-Ali ............... A61B 5/6838
600/323
9,687,162 B2 * 6/2017 Vetter ............... A61B 5/14552
(Continued)

FOREIGN PATENT DOCUMENTS

KR 10-2017-0087896 A 7/2017
KR 10-1922221 B1 11/2018
(Continued)

OTHER PUBLICATIONS

Anand Chandrasekhar et al. "Smartphone-based blood pressure monitoring via the oscillometric finger-pressing method" Sci Transl Med., vol. 10, Mar. 7, 2018, (24 pages total).
(Continued)

*Primary Examiner* — Benjamin S Melhus
*Assistant Examiner* — Samuel C Kim
(74) *Attorney, Agent, or Firm* — Sughrue Mion, PLLC

(57) ABSTRACT

An apparatus for estimating bio-information, the apparatus including a pulse wave sensor and a processor. The pulse wave sensor includes a plurality of channels, each channel of the plurality of channels being configured to measure a first pulse wave signal of a first wavelength and a second pulse wave signal of a second wavelength that is different from the first wavelength. The processor is configured to: for each channel of the plurality of channels, generate a first oscillogram based on the first pulse wave signal, generate a second oscillogram based on the second pulse wave signal, and convert a phase delay between the first oscillogram and the second oscillogram into an area. The processor is further configured to determine a channel among the plurality of channels based on the area of each channel, and estimate bio-information based on the determined channel.

17 Claims, 18 Drawing Sheets

(51) Int. Cl.
*A61B 5/022* (2006.01)
*A61B 5/024* (2006.01)

(56) References Cited

U.S. PATENT DOCUMENTS

| | | | |
|---|---|---|---|
| 10,354,118 B2 | 7/2019 | Li et al. | |
| 2002/0026121 A1* | 2/2002 | Kan | A61B 5/02255 600/500 |
| 2006/0009700 A1* | 1/2006 | Brumfield | A61B 5/6838 600/587 |
| 2007/0299323 A1* | 12/2007 | Arns | A61B 5/14532 600/301 |
| 2008/0091121 A1* | 4/2008 | Sun | A61B 5/0059 600/587 |
| 2009/0240125 A1* | 9/2009 | Such | A61B 5/6826 600/323 |
| 2009/0324033 A1 | 12/2009 | Addison et al. | |
| 2010/0076282 A1* | 3/2010 | Sandmore | A61B 5/6843 600/587 |
| 2010/0198027 A1* | 8/2010 | Dixon | A61B 5/412 600/323 |
| 2011/0270579 A1 | 11/2011 | Watson et al. | |
| 2012/0029320 A1* | 2/2012 | Watson | A61B 5/02416 600/301 |
| 2013/0172703 A1* | 7/2013 | Dixon | A61B 5/14551 600/339 |
| 2013/0172767 A1 | 7/2013 | Dripps et al. | |
| 2013/0317331 A1* | 11/2013 | Bechtel | A61B 5/1455 600/323 |
| 2015/0223700 A1 | 8/2015 | Kirenko | |
| 2017/0172430 A1* | 6/2017 | Zhao | A61B 5/02028 |
| 2017/0202493 A1 | 7/2017 | Bezemer | |
| 2019/0110758 A1 | 4/2019 | Kang et al. | |
| 2020/0008693 A1 | 1/2020 | Mukkamala et al. | |
| 2020/0229743 A1 | 7/2020 | Choi et al. | |
| 2020/0375478 A1* | 12/2020 | Bremer | A61B 5/0082 |

FOREIGN PATENT DOCUMENTS

| | | |
|---|---|---|
| KR | 10-2019-0043464 A | 4/2019 |
| KR | 10-2019-0081527 A | 7/2019 |
| KR | 10-2019-0119382 A | 10/2019 |

OTHER PUBLICATIONS

Communication issued Jan. 7, 2022 by the European Patent Office in European Patent Application No. 21185287.6.

* cited by examiner

APPARATUS AND METHOD FOR ESTIMATING BIO-INFORMATION

CROSS-REFERENCE TO RELATED APPLICATION(S)

This application claims priority from Korean Patent Application No. 10-2020-0127934, filed on Oct. 5, 2020, in the Korean Intellectual Property Office, the entire disclosure of which is incorporated by reference herein for all purposes.

BACKGROUND

1. Field

Example embodiments of the present disclosure relate to an apparatus and a method for estimating bio-information, and more particularly to extracting a cardiovascular characteristic without using a cuff and estimating bio-information based on the extracted cardiovascular characteristic.

2. Description of the Related Art

General techniques for extracting cardiovascular characteristics, such as blood pressure and the like, without using a pressure cuff include a pulse wave analysis (PWA) method and a pulse wave velocity (PWV) method.

The PWA method is a method of extracting cardiovascular characteristics by analyzing the shape of a photoplethysmography (PPG) signal or a body surface pressure signal obtained from a peripheral part of the body, e.g., a fingertip, a radial artery, or the like. The blood ejected from the left ventricle causes reflection at areas of large branches, such as the renal arteries and the iliac arteries, and the reflection affects the shape of the pulse wave or body pressure wave measured at the peripheral part of the body. Thus, by analyzing this shape, arterial stiffness, arterial age, aortic artery pressure waveform of the like can be inferred.

The PWV method is a method of extracting cardiovascular characteristics, such as arterial stiffness, blood pressure, or the like, by measuring a pulse wave transmission time. In this method, a delay (a pulse transit time (PTT)) between an R-peak (left ventricular contraction interval) of an electrocardiogram (ECG) and a peak of a PPG signal obtained from a peripheral part of the body, e.g., a finger or the radial artery is measured by measuring the ECG and PPG signals of the peripheral part of the body and a velocity at which the blood from the heart reaches the peripheral part of the body is calculated by dividing an approximate length of the arm by the PTT.

SUMMARY

In accordance with an aspect of an example embodiment, there is provided an apparatus for estimating bio-information, the apparatus including: a pulse wave sensor including a plurality of channels, each channel of the plurality of channels being configured to measure a first pulse wave signal of a first wavelength and a second pulse wave signal of a second wavelength that is different from the first wavelength; and a processor configured to: for each channel of the plurality of channels, generate a first oscillogram based on the first pulse wave signal, generate a second oscillogram based on the second pulse wave signal, and convert a phase delay between the first oscillogram and the second oscillogram into an area; and determine a channel among the plurality of channels based on the area of each channel, and estimate bio-information based on the determined channel.

The pulse wave sensor may include at least one light source configured to emit light of the first wavelength and light of the second wavelength onto an object; and at least one light receiver configured to detect the light of the first wavelength and the light of the second wavelength, which is scattered or reflected from the object.

The at least one light receiver may include at least one of a photodiode array or a complementary metal-oxide semiconductor (CMOS) image sensor.

The processor may be further configured to convert the phase delay between the first oscillogram and the second oscillogram into the area in a Lissajous waveform.

The processor may be further configured to determine the channel based on at least one of a size of the area, a slope of the Lissajous waveform, a shape of the area, or a ratio between a first region and a second region, the first region and the second region being obtained by dividing the area of each channel.

The processor may be further configured to exclude, from the determined channel, a channel, which does not satisfy a predetermined criterion, based on the first oscillogram and the second oscillogram of each channel.

The processor may be further configured to: generate, for each channel, a third oscillogram by subtracting the second oscillogram from the first oscillogram; and exclude, from the determined channel, a channel based on at least one of a full width at half maximum (FWHM) in the third oscillogram, a full width at a point corresponding to a predetermined ratio between a baseline point and a maximum point of the third oscillogram, or a statistical value of residuals between a pulse wave before curve fitting of the third oscillogram and a pulse wave after the curve fitting of the third oscillogram.

The processor may be further configured to determine a difference coefficient based on the first wavelength and the second wavelength, and subtract the second oscillogram, to which the difference coefficient is applied, from the first oscillogram.

The apparatus may further include a force/pressure sensor configured to measure a contact force and/or a contact pressure exerted between an object and the pulse wave sensor.

The processor may be further configured to estimate the bio-information by using the first oscillogram of the determined channel, the second oscillogram of the determined channel, or a third oscillogram generated by subtracting the second oscillogram of the determined channel from the first oscillogram of the determined channel.

The processor may be further configured to estimate first bio-information by using the first oscillogram, estimate second bio-information by using the second oscillogram, and obtain final bio-information based on at least one of the first bio-information or the second bio-information.

The processor may be further configured to determine two or more channels among the plurality of channels based on the area of each channel, estimate bio-information values of respective determined two or more channels, and obtain final bio-information by using at least one of the estimated bio-information values of the respective determined two or more channels.

The bio-information may include at least one of a blood pressure, a vascular age, an arterial stiffness, an aortic pressure waveform, a vascular compliance, a stress index, a fatigue level, a skin age, or a skin elasticity.

In accordance with an aspect of an example embodiment, there is provided a method of estimating bio-information, the method including: by using a pulse wave sensor having a plurality of channels, measuring, for each channel of the plurality of channels, a first pulse wave signal of a first wavelength and a second pulse wave signal of a second wavelength, the second wavelength being different from the first wavelength; generating, for each channel of the plurality of channels, a first oscillogram based on the first pulse wave signal and generating a second oscillogram based on the second pulse wave signal; converting, for each channel of the plurality of channels, a phase delay between the first oscillogram and the second oscillogram into an area; determining a channel among the plurality of channels based on the area of each channel; and estimating bio-information based on the determined channel.

The method may further include converting the phase delay between the first oscillogram and the second oscillogram into the area in a Lissajous waveform.

The determining may include determining the channel based on at least one of a size of the area, a slope of the Lissajous waveform, a shape of the area, or a ratio between a first region and a second region, the first region and the second region being obtained by dividing the area of each channel.

The method may further include excluding, from the determined channel, a channel, which does not satisfy a predetermined criterion, based on the first oscillogram and the second oscillogram of each channel.

The method may further include: generating, for each channel, a third oscillogram by subtracting the second oscillogram from the first oscillogram; and excluding, from the determined channel, a channel based on at least one of a full width at half maximum (FWHM) in the third oscillogram, a full width at a point corresponding to a predetermined ratio between a baseline point and a maximum point of the third oscillogram, or a statistical value of residuals between a pulse wave before curve fitting of the third oscillogram and a pulse wave after the curve fitting of the third oscillogram.

The estimating may include estimating the bio-information by using the first oscillogram of the determined channel, the second oscillogram of the determined channel, or a third oscillogram generated by subtracting the second oscillogram of the determined channel from the first oscillogram of the determined channel.

The estimating may include estimating first bio-information by using the first oscillogram of the determined channel, estimating second bio-information by using the second oscillogram of the determined channel, and obtaining final bio-information based on at least one of the first bio-information or the second bio-information.

The estimating may include determining two or more channels among the plurality of channels based on the area of each channel, estimating bio-information values of respective determined two or more channels, and obtaining final bio-information by using at least one of the estimated bio-information values of the respective determined two or more channels.

In accordance with an aspect of an example embodiment, there is provided an apparatus for estimating bio-information, the apparatus including: a pulse wave sensor having a plurality of channels, each channel of the plurality of channels being configured to measure a first pulse wave signal of a first wavelength and a second pulse wave signal of a second wavelength that is different from the first wavelength; and a processor configured to: obtain, for each channel, obtain a first feature value based on an alternating current (AC) component and a direct current (DC) component of the first pulse wave signal and an AC component and a DC component of the second pulse wave signal; determine a channel among the plurality of channels based on the obtained first feature value of each channel; and estimate bio-information based on the determined channel.

The processor may be further configured to obtain the first feature value for each channel based on a ratio between the AC component and the DC component of the first pulse wave signal and a ratio between the AC component and the DC component of the second pulse wave signal.

The processor may be further configured to generate an oscillogram based on at least one of the first pulse wave signal or the second pulse wave signal of the determined channel, obtain a second feature value by using the generated oscillogram, and estimate the bio-information based on at least one of the first feature value or the second feature value.

In accordance with an aspect of an example embodiment, there is provided a method of estimating bio-information, the method including: by using a pulse wave sensor having a plurality of channels, measuring, for each channel of the plurality of channels, a first pulse wave signal of a first wavelength and a second pulse wave signal of a second wavelength that is different from the first wavelength; obtaining, for each channel, a first feature value based on an alternating current (AC) component and a direct current (DC) component of the first pulse wave signal and an AC component and a DC component of the second pulse wave signal; determining a channel among the plurality of channels based on the obtained first feature value of each channel; and estimating bio-information based on the determined channel.

The obtaining may include obtaining the first feature value for each channel based on a ratio between the AC component and the DC component of the first pulse wave signal and a ratio between the AC component and the DC component of the second pulse wave signal.

The estimating may include: generating an oscillogram based on at least one of the first pulse wave signal or the second pulse wave signal of the determined channel; obtaining a second feature value by using the generated oscillogram; and estimating the bio-information based on at least one of the first feature value or the second feature value.

BRIEF DESCRIPTION OF THE DRAWINGS

The above and other aspects will become more apparent by describing in detail example embodiments with reference to the attached drawings, in which.

DETAILED DESCRIPTION

Figure 1A:
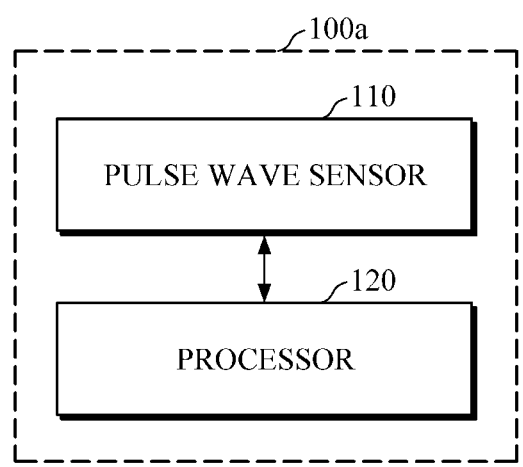
FIGS. 1A and 1B are block diagrams illustrating an apparatus for estimating bio-information according to example embodiments.

Details of example embodiments are included in the following detailed description and drawings. Advantages and features of the disclosure, and a method of achieving the same will be more clearly understood from the following embodiments described in detail with reference to the accompanying drawings. Throughout the drawings and the detailed description, unless otherwise described, the same drawing reference numerals will be understood to refer to the same elements, features, and structures.

It will be understood that, although the terms first, second, etc. may be used herein to describe various elements, these elements should not be limited by these terms. These terms are only used to distinguish one element from another. Also, the singular forms are intended to include the plural forms as well, unless the context clearly indicates otherwise. It will be further understood that when an element is referred to as "comprising" another element, the element is intended not to exclude one or more other elements, but to further include one or more other elements, unless explicitly described to the contrary. In the following description, terms such as "unit" and "module" indicate a unit for processing at least one function or operation and they may be implemented by using hardware, software, or a combination thereof.

Hereinafter, embodiments of an apparatus and method for estimating bio-information will be described in detail with reference to the accompanying drawings.

Figure 1B:
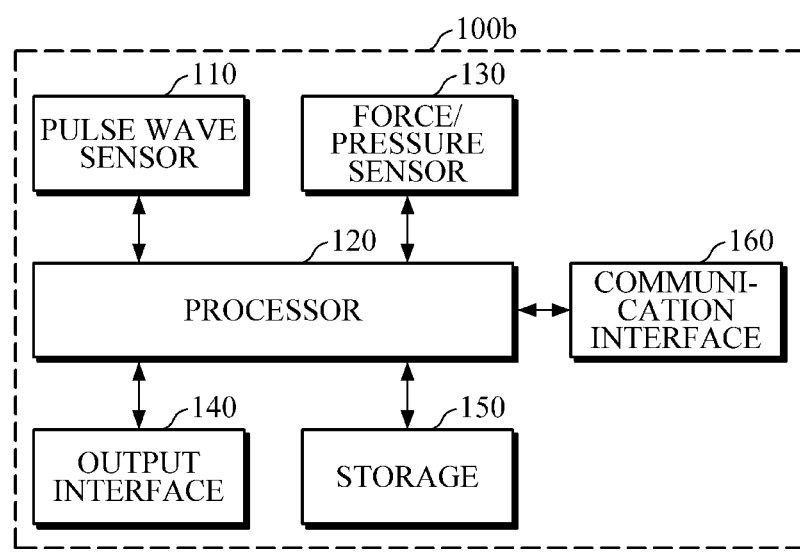
Figure 2A:
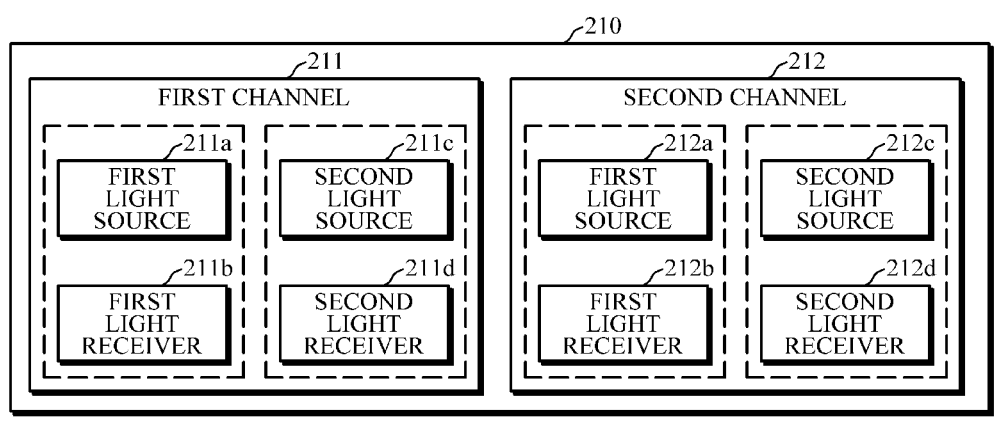
FIGS. 2A and 2B are diagrams illustrating examples of a configuration of a pulse wave sensor of an apparatus for estimating bio-information according to example embodiments.
Figure 2B:
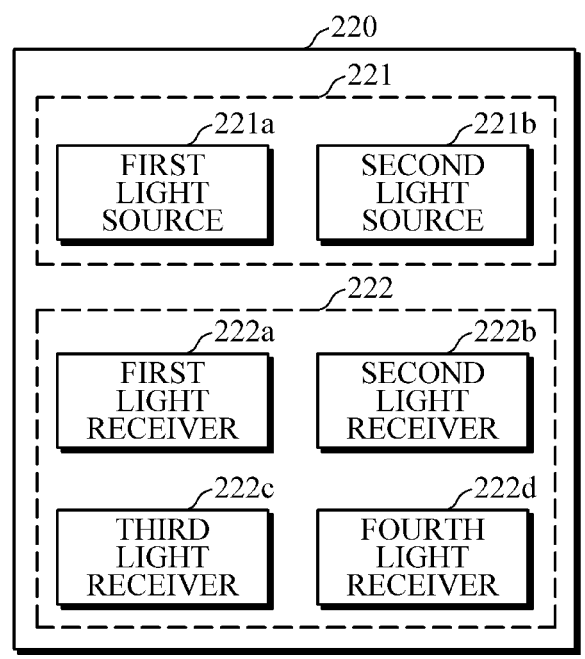

FIGS. 1A and 1B are block diagrams illustrating an apparatus for estimating bio-information according to example embodiments. FIGS. 2A and 2B are diagrams illustrating examples of a configuration of a pulse wave sensor of an apparatus for estimating bio-information according to example embodiments.

Apparatuses 100a and 100b for estimating bio-information according to the embodiments as shown in FIGS. 1A and 1B may be embedded in a terminal, such as a smartphone, a tablet PC, a desktop computer, a laptop computer, and the like, or may be manufactured as an independent hardware device. When the apparatuses 100a and 100b are manufactured as an independent hardware device, the hardware device may be implemented as a wearable device to be worn on an object OBJ of a user so that a user may easily measure bio-information of the user while carrying the wearable device. Examples of the wearable device may include a wristwatch-type wearable device, a bracelet-type wearable device, a wristband-type wearable device, a ring-type wearable device, a glasses-type wearable device, a headband-type wearable device, or the like, but the wearable device is not limited thereto, and may be modified for various purposes, such as a fixed type device and the like used in medical institutions for measuring and analyzing bio-information.

Referring to FIG. 1A, the apparatus 100a for estimating bio-information includes a pulse wave sensor 110 and a processor 120.

The pulse wave sensor 110 measures a photoplethysmography (PPG) signal (hereinafter referred to as a "pulse wave signal") from an object. The object may be a body area which may come into contact with the pulse wave sensor 110, and may be a body part at which pulse waves may be easily measured based on PPG signals. For example, the object may be a finger where blood vessels are densely located, but the object is not limited thereto and may be any other part of a body, such as an area on a wrist that is adjacent to a radial artery, or a peripheral part of the body, such as an upper portion of the wrist, toes, etc., where veins or capillaries are located.

The pulse wave sensor 110 may include a plurality of light sources for emitting light onto the object, and one or more light receivers which are disposed at positions spaced apart from the light sources by a predetermined distance and detect light scattered or reflected from the object. At least some of the plurality of light sources may emit light of different wavelengths. The plurality of light sources may include a light emitting diode (LED), a laser diode (LD), a phosphor, etc., but are not limited thereto. Further, the plurality of light receivers may include a photodiode, a photodiode array, a complementary metal-oxide semiconductor (CMOS) image sensor, a charge-coupled device (CCD) image sensor, and the like.

The pulse wave sensor 110 may have multiple channels to measure a plurality of pulse wave signals at multiple points of the object. The channels of the pulse wave sensor 110 may be arranged in a predetermined shape such as a circular shape, an oval shape, a linear shape, etc., so as to measure pulse wave signals at multiple points of the object. Each channel of the pulse wave sensor 110 may include light sources and light receivers, which may be shared by two or more channels. Further, each channel may detect pulse wave signals having a plurality of wavelengths.

Referring to FIG. 2A, a pulse wave sensor 210 according to an embodiment may have a first channel 211 for measuring a pulse wave signal at a first point of the object, and a second channel 212 for measuring a pulse wave signal at a second point of the object. A first light source 211a corresponding to the first channel 211 and a first light source 212a corresponding to the second channel 212 and a first light receiver 211b corresponding to the first channel 211 and a first light receiver 212b corresponding to the second channel 212 may have a size in a range of 3 mm to 10 mm, but their size is not limited thereto.

The first channel 211 and the second channel 212 may respectively include the first light source 211a and the first light source 212a configured to emit light of a first wavelength and the first light receiver 211b and the first light receiver 212b configured to detect light scattered or reflected from the object after light is emitted by the first light sources 211a and 212a onto the object. Further, the first channel 211 and the second channel 212 may respectively include a second light source 211c and a second light resource 212c configured to emit light of a second wavelength and a second light receiver 211d and a second light receiver 212d configured to detect light scattered or reflected from the object after light is emitted by the second light sources 211c and 212c onto the object. The first wavelength and the second wavelength may be different from each other, and may include, for example, an infrared wavelength, a green wavelength, a blue wavelength, and/or a red wavelength.

For convenience of explanation, FIG. 2A illustrates two channels 211 and 212, each including a pair of two light sources and a pair of two light receivers. However, this is merely for convenience of explanation, and the channels are not limited thereto and may be provided in various numbers and configurations according to the size and shape of a form factor, and the like. For example, each of the channels 211 and 212 may include a plurality of light sources for emitting light of a plurality of wavelengths and one light receiver, such that the plurality of light sources may be driven sequentially and pulse wave signals may be measured sequentially by the one light receiver. In addition, each of the channels 211 and 212 may include only one light source and one light receiver, in which case a color filter may be disposed on a front surface of the light source or the light receiver to pass or detect different wavelengths.

Referring to FIG. 2B, a pulse wave sensor 220 according to another example embodiment may include a group 221 of light sources and a group 222 of light receivers. That is, the pulse wave sensor 220 may include a first light source 221a and a second light source 221b, and a first light receiver 222a, a second light receiver 222b, a third light receiver 222c, and a fourth light receiver 222d. The first light source 221a, the first light receiver 222a, and the second light receiver 222b may form a first channel 221a for measuring a pulse wave signal at a first point of the object, and the second light source 221b, the third light receiver 222c, and the fourth light receiver 222d may form a second channel 222 for measuring a pulse wave signal at a second point of the object. For convenience of explanation, the pulse wave sensor 220 has two channels, but is not limited thereto.

Each of the first light source 221a and the second light source 221b may emit light of different wavelengths, e.g., by using a color filter. For example, the first and the second light sources 221a and 221b may emit light of an infrared wavelength, a green wavelength, a blue wavelength, a red wavelength, and the like. The first through the fourth light receivers 222a-222d may respectively detect light of different wavelengths that is scattered or reflected from the object after the light from the first and the second light sources 221a and 221b is emitted onto the object. While two light sources and four light receivers included in two channels are shown in FIG. 2B, the number of the light sources and the light receivers is not particularly limited, and one channel may include, for example, two light sources configured to emit light of different wavelengths onto the object and one light receiver which may be shared by the two light sources and detect light scattered or reflected from the object.

Various embodiments of the structure of the pulse wave sensor 110 of FIG. 1 are described above with reference to FIGS. 2A and 2B. However, these are merely examples, and the structure is not particularly limited to the above examples, and in order to detect pulse wave signals at multiple points of the object, various numbers and arrangements of the channels, light sources, and light receivers may be provided according to the position of the object and the size and shape of a form factor, and the like.

Referring back to FIG. 1A, the processor 120 may sequentially or simultaneously control each of the channels in a time division manner. Further, in a case where each channel includes a plurality of light sources of different wavelengths, the processor 120 may drive the light sources in the order of from short to long wavelengths, or vice versa. In this case, driving conditions of the light sources, e.g., a driving sequence and a current strength of light sources, a pulse duration, etc., may be pre-defined.

In addition, the processor 120 may estimate bio-information by using pulse wave signals measured at multiple points of the object by the respective channels of the pulse wave sensor 110. Once pulse wave signals are obtained by the respective channels of the pulse wave sensor 110, the processor 120 may select a channel for estimating bio-information by using the obtained pulse wave signals, and may estimate bio-information based on a pulse wave signal of the selected channel. Hereinafter, for description purposes, the selected channel may be referred to as an optimal channel. In this case, the bio-information may include blood pressure, vascular age, arterial stiffness, aortic pressure waveform, skin elasticity, skin age, stress index, fatigue level, etc., but is not limited thereto. For convenience of explanation, the following description will be given using blood pressure as an example.

Referring to FIG. 1B, the apparatus 100b for estimating bio-information according to another embodiment includes the pulse wave sensor 110, the processor 120, a force/pressure sensor 130, an output interface 140, a storage 150, and a communication interface 160.

The pulse wave sensor 110 may have multiple channels to measure a plurality of pulse wave signals at multiple points of the object. As described above, each of the channels may be provided in various manners to detect pulse wave signals having two or more wavelengths.

The processor 120 may determine an optimal channel for estimating bio-information based on the pulse wave signals obtained by the respective channels, and may estimate bio-information by using a pulse wave signal of the determined optimal channel.

When a user places an object on the pulse wave sensor 110 for a predetermined period of time and increases or decreases a pressing force to measure a pulse wave signal, the force/pressure sensor 130 may measure a contact force and/or contact pressure between the object and the pulse wave sensor 110. The force/pressure sensor 130 may be formed as a single force sensor, a force sensor array, one or more pressure sensors, or a combination of a force sensor and an area sensor. The force/pressure sensor 130 may include a strain gauge and the like, but is not limited thereto. The contact force and/or contact pressure measured by the force/pressure sensor 130 may be used along with the pulse wave signals, obtained by the respective channels, to generate oscillograms and to estimate bio-information.

Upon receiving a request for estimating bio-information from a user, the processor 120 may guide the user on a contact state with respect to the pulse wave sensor 110. For example, upon receiving the request for estimating bio-information, the processor 120 may obtain, from the storage 150, a reference pressure to be applied by the object to the pulse wave sensor 110, and may guide the user on the obtained reference pressure through the output interface 140. Further, the processor 120 may guide the user in real time on contact pressure based on a contact force and/or contact pressure which are measured in real time by the force/pressure sensor 130 while the pulse wave signal is measured.

The output interface 140 may output and provide the pulse wave signal measured by the pulse wave sensor 110 and/or a processing result of the processor 120 to the user. The output interface 140 may provide information by various visual/non-visual methods using a display module, a speaker, a haptic device, and the like mounted in the apparatus 100b.

For example, the output interface 140 may output the measured pulse wave signal, the oscillogram of each channel, and the like in the form of graphs. Further, the output interface 140 may visually display an estimated bio-information value of a user by using various visual methods, such as by changing color, line thickness, font, and the like based on whether the estimated blood pressure value falls within or outside a normal range. Additionally or alternatively, the output interface 140 may output the estimated bio-information value by voice and/or vibrations, tactile sensation, and the like based on whether the estimated bio-information value is abnormal or not, so that the user may easily recognize abnormality in the user's health condition. Alternatively, upon comparing the estimated bio-information value with a previous estimation history, based on a determination that the estimated bio-information value is abnormal, the output interface 140 may provide a warning message, an alarm signal, and the like, as well as guide information on a user's action such as information on food that the user should be careful about, related hospital information, and the like.

The storage 150 may store a variety of information related to estimating bio-information, and information such as the obtained pulse wave signals and oscillograms, the estimated bio-information values, and the like. Further, the storage 150 may store light source driving conditions, a contact pressure conversion model, a blood pressure estimation model, conditions for excluding channels, conditions for determining an optimal channel, and the like. In addition, the storage 150 may store user characteristics information such as a user's age, gender, health condition, and the like. However, the information stored in the storage 150 is not limited thereto.

The storage 150 may include at least one storage medium of a flash memory type memory, a hard disk type memory, a multimedia card micro type memory, a card type memory (e.g., a secure digital (SD) memory, an eXtreme digital (XD) memory, etc.), a Random Access Memory (RAM), a Static Random Access Memory (SRAM), a Read Only Memory (ROM), an Electrically Erasable Programmable Read Only Memory (EEPROM), a Programmable Read Only Memory (PROM), a magnetic memory, a magnetic disk, and an optical disk, and the like, but is not limited thereto.

The communication interface 160 may communicate with an external device by using communication techniques under the control of the processor 120, and may receive data used for estimating bio-information from the external device and/or may transmit a processing result of the processor 120 to the external device. The external device may include a smartphone, a tablet PC, a wearable device, a cuff manometer, and the like.

In this case, examples of the communication techniques may include Bluetooth communication, Bluetooth Low Energy (BLE) communication, Near Field Communication (NFC), WLAN communication, Zigbee communication, Infrared Data Association (IrDA) communication, Wi-Fi Direct (WFD) communication, Ultra-Wideband (UWB) communication, Ant+ communication, WIFI communication, Radio Frequency Identification (RFID) communication, 3G communication, 4G communication, 5G communication, and the like. However, this is merely exemplary and is not intended to be limiting.

Figure 3:
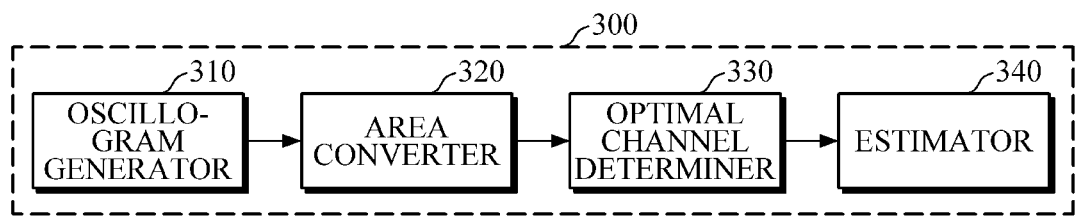
FIG. 3 is a diagram illustrating a configuration of a processor included in an apparatus for estimating bio-information according to an example embodiment.
Figure 4A:
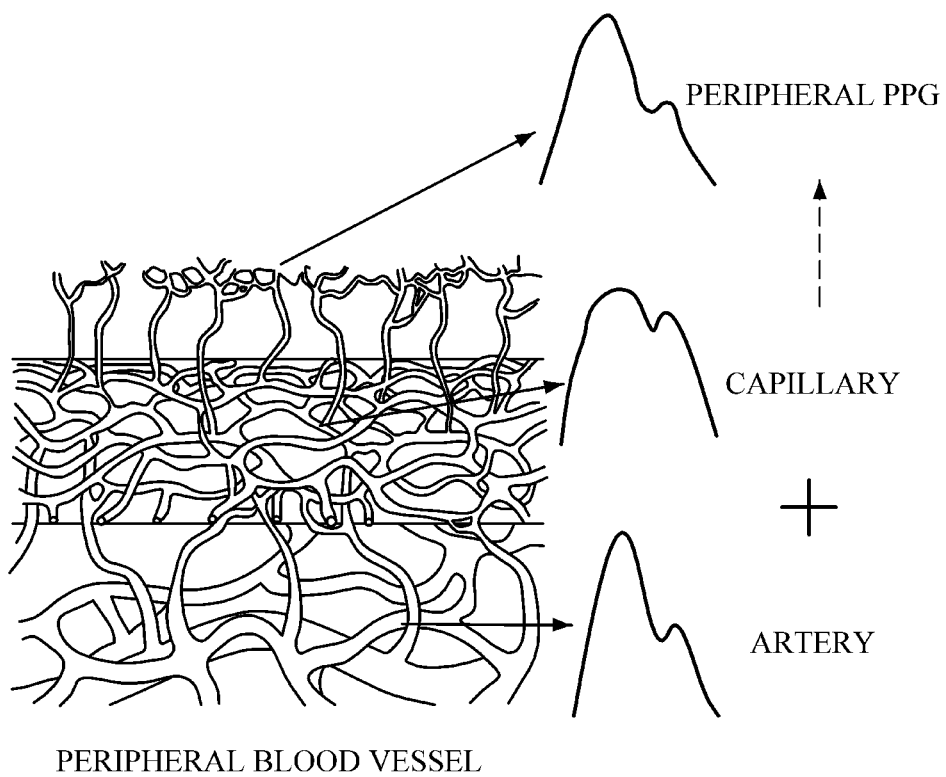
FIGS. 4A and 4B are diagrams explaining an example of a general method of estimating bio-information.
Figure 4B:
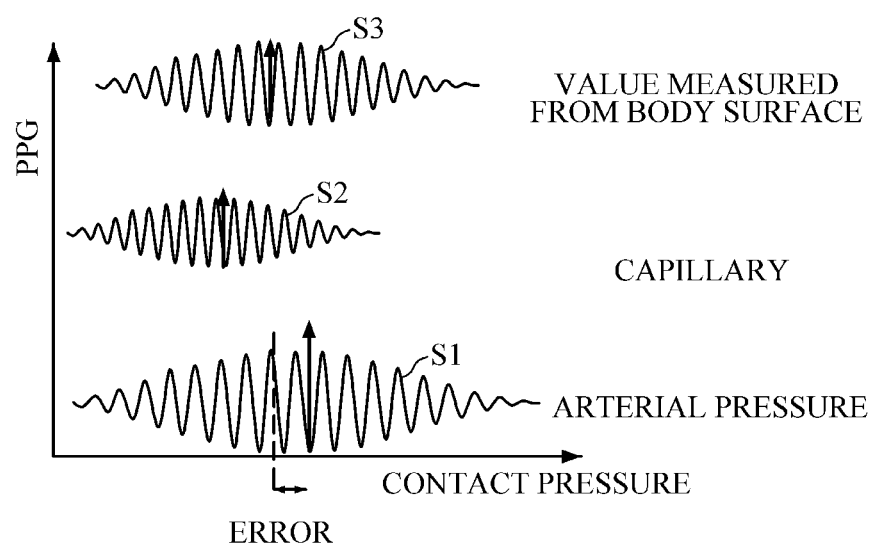
Figure 5A:
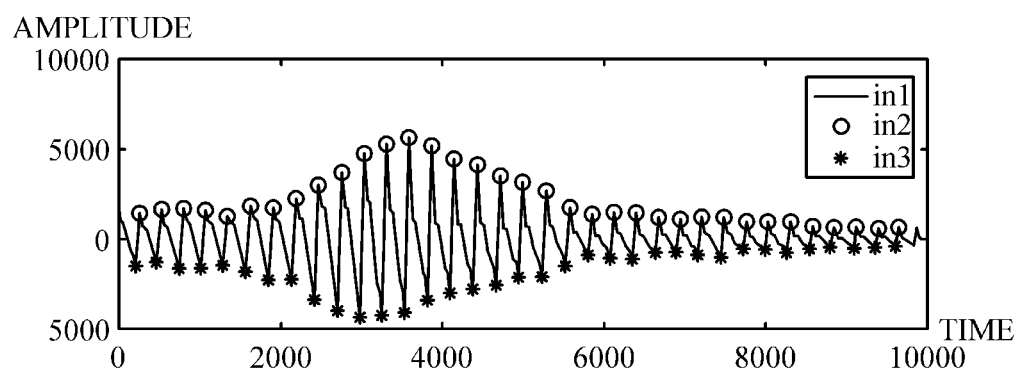
FIGS. 5A and 5B are diagrams explaining an example of generating oscillograms.
Figure 5B:
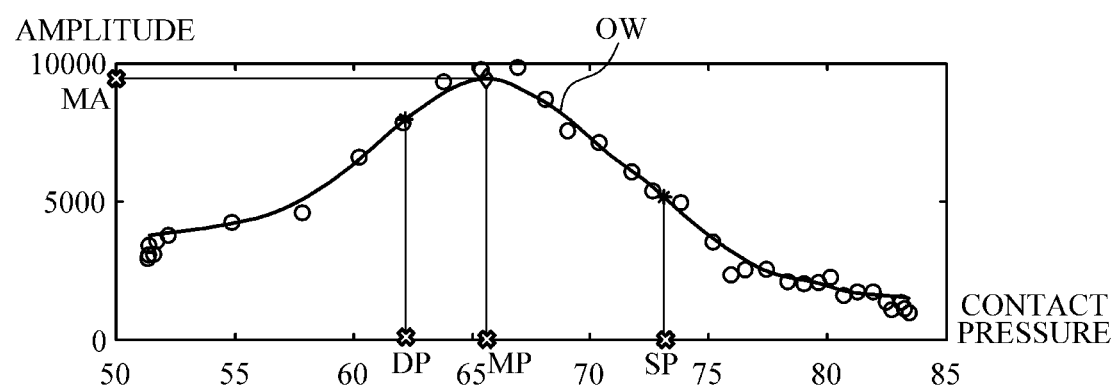
Figure 6A:
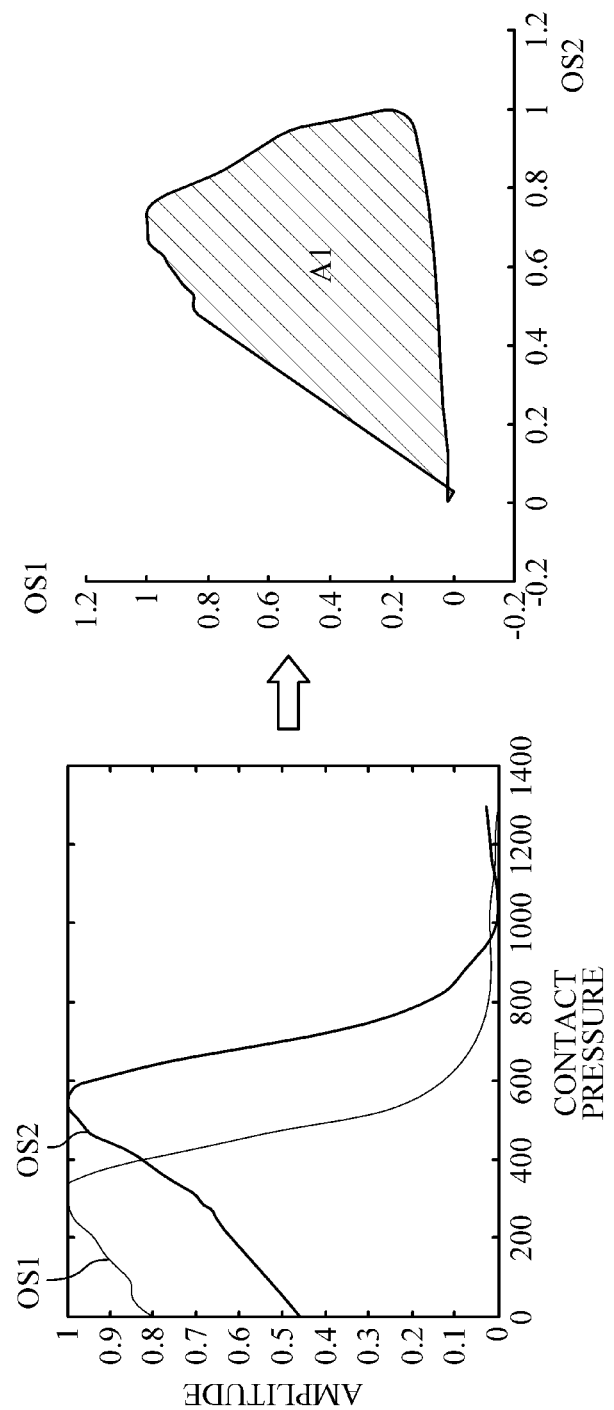
FIGS. 6A, 6B, and 6C are diagrams explaining examples of selecting an optimal channel according to an example embodiment.
Figure 6B:
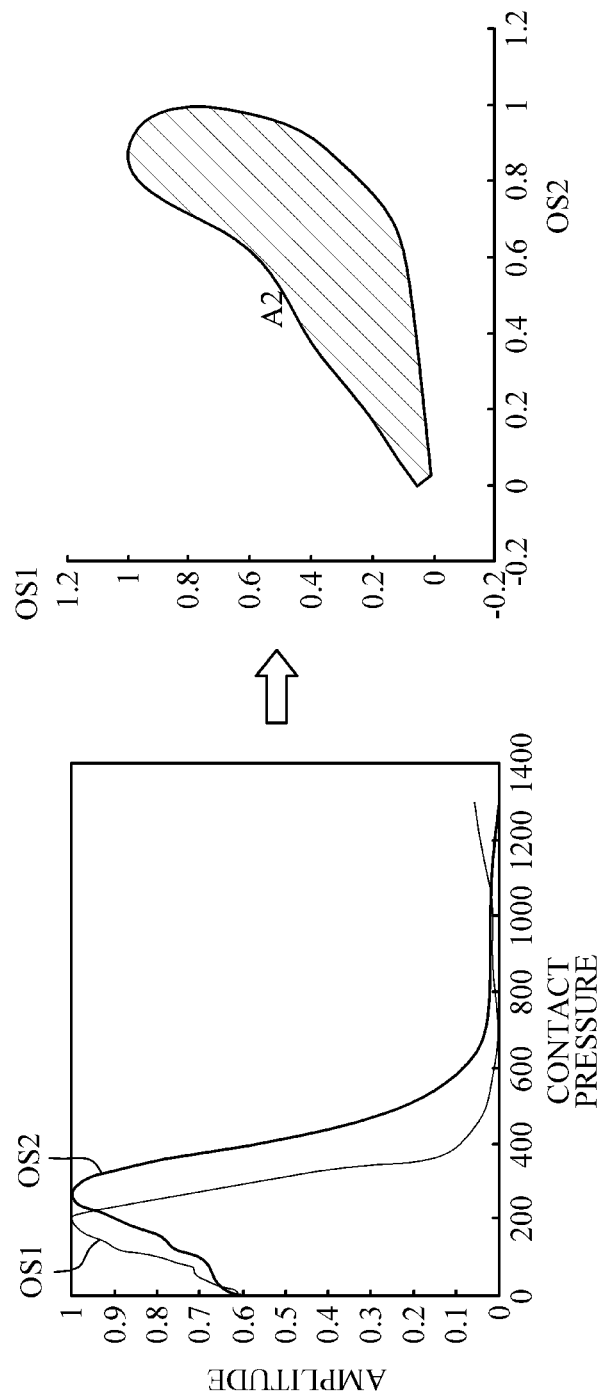
Figure 6C:
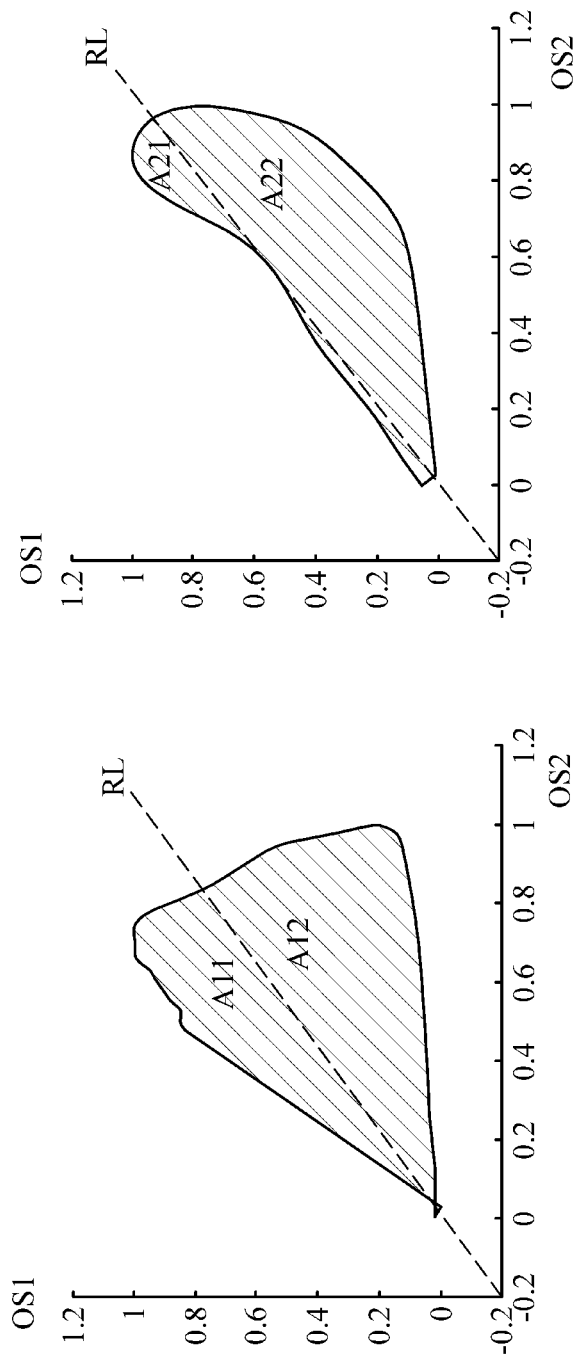

FIG. 3 is a diagram illustrating an example of a configuration of the processor 120 of the apparatuses 100a and 100b for estimating bio-information illustrated in FIGS. 1A and 1B. FIGS. 4A and 4B are diagrams explaining an example of a general method of estimating bio-information. FIGS. 5A and 5B are diagrams explaining an example of generating oscillograms according to an example embodiment. FIGS. 6A to 6C are diagrams explaining examples of selecting an optimal channel according to an example embodiment.

Referring to FIG. 4A, an apparatus for measuring blood pressure without a cuff generally measures blood pressure by using photoplethysmography (PPG) signals. In this case, a pulse wave sensor comes into contact with a body surface at various pressure levels, and estimates blood pressure by measuring pulse wave signals at each contact pressure level and by obtaining mean arterial pressure (MAP) of local blood vessels. In this case, the PPG signals, measured by the pulse wave sensor from the body surface, may be observed as a combination of arterial pulse wave signals, generated at great depths from the body surface, and capillary pulse wave signals generated at relatively shallow depths from the body surface. Here, the capillary pulse wave signals may act as noise in estimating blood pressure using oscillometry.

Referring to FIG. 4B, a pulse wave signal at the bottom of the graph represents an arterial pulse wave signal S1; a pulse wave signal at the center of the graph represents a capillary pulse wave signal S2; and a pulse wave signal at the top of the graph represents a peripheral pulse wave signal S3 measured from the body surface. As the peripheral pulse wave signal S3 is represented by a combination of the arterial pulse wave signal S1 and the capillary pulse wave signal S2, it can be seen that a maximum amplitude point associated with blood pressure is moved from an arrow point of the arterial pulse wave signal S1 to an arrow point of the peripheral pulse wave signal S3. This shows that accuracy may be reduced when blood pressure is measured using oscillometry. That is, a value measured from the body surface includes an error value added to an arterial blood pressure value, thereby resulting in a difference from accurate blood pressure values.

Accordingly, in order to solve the above problem that accuracy of estimation is reduced when oscillometry is performed at a peripheral body part using a pulse wave signal having a relatively short wavelength, an example embodiment provides a method of improving accuracy in estimating bio-information by selecting a channel, which measures a pulse wave signal from a blood vessel at a relatively deep depth, among multiple channels of multiple pulse wave signals.

Referring to FIG. 3, a processor 300 according to an embodiment includes an oscillogram generator 310, an area converter 320, an optimal channel determiner 330, and an estimator 340.

Once a first pulse wave signal and a second pulse wave signal, having different wavelengths, are obtained by each channel, the oscillogram generator 310 may generate a first oscillogram and a second oscillogram based on the first pulse wave signal and the second pulse wave signal. The oscillogram generator 310 may generate oscillograms by using a correlation between a change in contact pressure, applied by the object to the pulse wave sensor 110, and a change in an amplitude of the pulse wave signal of each channel. In this case, the contact force and/or contact pressure obtained by the force/pressure sensor 130 of FIG. 1B may be used to obtain the change in contact pressure. Alternatively, in a case where the force/pressure sensor 130 is not included as illustrated in FIG. 1A, contact pressure may be obtained from an amplitude of the pulse wave signal by using a contact pressure conversion equation which defines a correlation between the amplitude of the pulse wave signal and the contact pressure.

FIG. 5A illustrates an example of a change in an amplitude of the pulse wave signal measured when the object, being in contact with the pulse wave sensor 110, gradually increases a pressing force on the pulse wave sensor 110. FIG. 5B illustrates an oscillogram OW representing a correlation between a change in contact pressure, applied by the object to the pulse wave sensor 110, and an amplitude of the pulse wave signal.

The oscillogram generator 310 may extract, e.g., a peak-to-peak point of the pulse wave signal waveform by subtracting a negative (−) amplitude value in3 from a positive (+) amplitude value in2 of a waveform envelope in1 at each measurement time of the pulse wave signal, and may obtain an oscillogram OW by plotting the peak-to-peak amplitude at each measurement time against the contact pressure value at a corresponding time and by performing, for example, polynomial curve fitting.

Once the oscillogram generator 310 generates, for each channel, a first oscillogram at a first wavelength and a second oscillogram at a second wavelength, the area converter 320 may obtain an area based on the generated first and second oscillograms. In this case, the first wavelength and the second wavelength may be different wavelengths.

For example, the area converter 330 may convert a phase delay between the first oscillogram and the second oscillogram into an area in a Lissajous waveform. In this case, the area converter 330 may normalize the first oscillogram and the second oscillogram. For example, the area converter 330 may normalize an amplitude of the second oscillogram based on an amplitude of the first oscillogram, or may normalize the first oscillogram and the second oscillogram by applying an absorbance-based model according to the Beer-Lambert Law.

Once the area is obtained for each channel, the optimal channel determiner 330 may determine an optimal channel based on the obtained area.

For example, FIG. 6A illustrates a phase delay, converted into an area A1, between a first oscillogram OS1 and a second oscillogram OS2 of a first channel. FIG. 6B illustrates a phase delay, converted into an area A2, between a first oscillogram OS1 and a second oscillogram OS2 of a second channel. The optimal channel determiner 330 may determine an optimal channel based on the converted areas as described above. For example, as the area A1 of the first channel is greater than the area A2 of the second channel, the optimal channel determiner 330 may determine a channel having a largest area, i.e., the first channel, as the optimal channel. Alternatively, the optimal channel determiner 330 may determine, as the optimal channel, a predetermined number of channels in an order of a size of the corresponding area, starting from the largest area.

In another example, the optimal channel determiner 330 may divide an area of each channel into two or more regions according to one or more criterions, and may determine an optimal channel based on an area ratio between the divided areas. For example, the optimal channel determiner 330 may determine, as the optimal channel, one or more channels in the order of a magnitude of the area ratio of each channel, starting from a highest area ratio. FIG. 6C illustrates an example of dividing an area of each channel based on a straight line RL having a slope of 1, however, the slope is not necessarily limited to 1. Further, it is not necessary to divide the area based on a straight line passing through the origin, and the area may be divided based on the center of gravity of each area or based on a straight line perpendicular to an X or Y axis and passing through any value on the X or Y axis. The method of dividing the area of each channel is not limited. The optimal channel determiner 330 may obtain, for the first channel, a first area ratio by dividing a first region A11, having a smaller area, by a second region A12 having a larger area; may obtain, for the second channel, a second area ratio by dividing a first region A21, having a smaller area, by a second region A22 having a larger area; and may determine a channel, having a greater area ratio of the first area ratio and the second area ratio, as the optimal channel.

In yet another example, the optimal channel determiner 330 may determine the optimal channel based on a shape of a Lissajous waveform including a slope of the Lissajous waveform of each channel. For example, the optimal channel determiner 330 may calculate a slope of the Lissajous waveform of each channel, and may determine a channel, in which the calculated slope satisfies a predetermined criterion, as the optimal channel. Alternatively, the optimal channel determiner 330 may calculate a similarity between an area shape of the Lissajous waveform and a reference area shape, and may determine one or more channels as the optimal channel in an order of a higher calculated similarity. However, the optimal channel is not limited thereto, and may be determined by analyzing the slope or an area shape of the Lissajous waveform by applying a model obtained based on machine learning, artificial intelligence, neural networks, and the like.

Further, based on the first oscillogram and the second oscillogram of each channel, the optimal channel determiner 330 may exclude a channel, which does not satisfy a predetermined criterion, in determining the optimal channel. For example, the optimal channel determiner 330 may generate a third oscillogram by using the first oscillogram at the first wavelength of each channel and the second oscillogram at the second wavelength of each channel, and may determine whether each channel satisfies a predetermined criterion based on the generated third oscillogram. For example, the optimal channel determiner 330 may determine a difference coefficient based on the first wavelength and the second wavelength, may apply the determined difference coefficient to the second oscillogram, and may generate the third oscillogram by subtracting the second oscillogram to which the difference coefficient is applied from the first oscillogram.

For example, if a full width at half maximum (FWHM) between a contact pressure at a baseline point and a contact pressure at a half-maximum point of the third oscillogram is greater than or equal to a predetermined threshold value, the optimal channel determiner 330 may exclude a corresponding channel. Alternatively, if a width at a point corresponding to a predetermined ratio between the baseline point and the maximum point of the third oscillogram is greater than or equal to a predetermined threshold value, or if a statistical value, e.g., a sum total, a mean value, a median value, and the like, of residuals between an actual pulse wave amplitude at a point corresponding to a predetermined contact pressure value and a pulse wave amplitude of the third oscillogram after curve fitting is greater than or equal to a predetermined threshold value, the optimal channel determiner 330 may exclude a corresponding channel. However, the exclusion of a channel is not limited thereto.

The estimator 340 may estimate bio-information by using an oscillogram of the optimal channel determined by the optimal channel determiner 330. For example, the estimator 340 may estimate blood pressure by using the first oscillogram or the second oscillogram of the optimal channel. For example, the first oscillogram or the second oscillogram may be an oscillogram at a relatively long wavelength. Alternatively, when the third oscillogram is generated by subtracting the second oscillogram from the first oscillogram of the optimal channel, the estimator 340 may estimate blood pressure by using the generated third oscillogram. In an example embodiment, a plurality of optimal channels may be determined, and the estimator 340 may estimate blood pressure for the respective optimal channels, and may combine the estimated blood pressure values to obtain a mean value, a median value, and the like of the blood pressure values of the respective optimal channels as a final blood pressure value.

Referring to FIG. 5B, the estimator 340 may estimate mean arterial pressure (MAP) based on a contact pressure value MP at a maximum point MA of the pulse wave in the third oscillogram. For example, the estimator 340 may determine, as MAP, the contact pressure value MP itself at the maximum point MA of the pulse wave. Alternatively, the estimator 340 may estimate MAP by applying the contact pressure value MP to a pre-defined MAP estimation equation. In this case, the MAP estimation equation may be expressed in the form of various linear or non-linear combination functions, such as addition, subtraction, division, multiplication, logarithmic value, regression equation, and the like, with no particular limitation.

Further, the estimator 340 may estimate diastolic blood pressure (DBP) and systolic blood pressure (SBP) based on contact pressure values DP and SP at points to the left and right of an amplitude value at the maximum point MA of the pulse wave and having a preset ratio, e.g., 0.5 to 0.7, to the amplitude value at the maximum point MA. Likewise, the estimator 340 may also determine the contact pressure values DP and SP to be DBP and SBP, respectively, or alternatively, may estimate DBP and SBP by using pre-defined DBP and SBP estimation equations, respectively.

Figure 7:
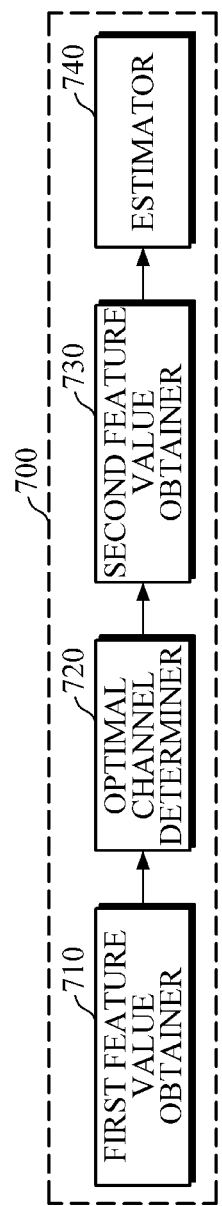
FIG. 7 is a diagram illustrating a configuration of a processor included in an apparatus for estimating bio-information according to an example embodiment.
Figure 8:
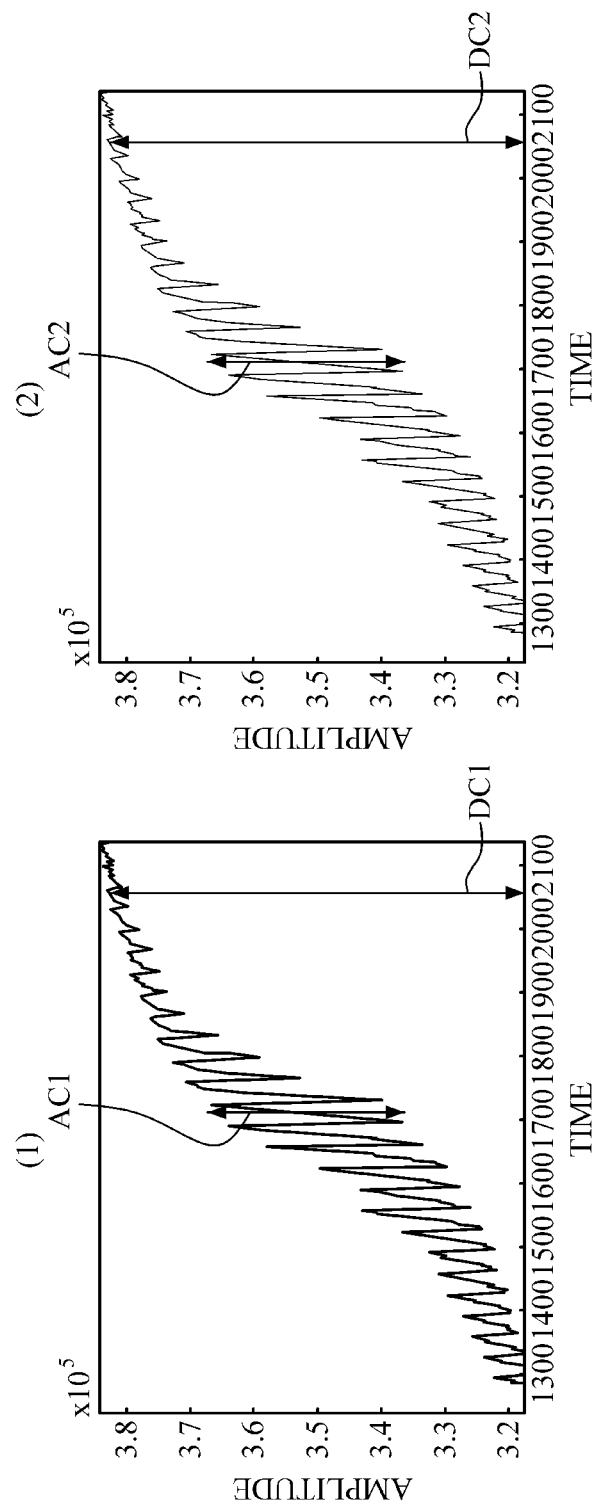
FIG. 8 is a diagram explaining an example of selecting an optimal channel according to an example embodiment.

FIG. 7 is a diagram illustrating another example of a configuration of the processor 120 of the apparatuses 100a and 100b for estimating bio-information according to the embodiments of FIGS. 1A and 1B. FIG. 8 is a diagram explaining another example of determining an optimal channel.

Referring to FIG. 7, a processor 700 according to an embodiment includes a first feature value obtainer 710, an optimal channel determiner 720, a second feature value obtainer 730, and an estimator 740.

As illustrated in FIG. 8, the first feature value obtainer 710 may obtain, for each channel, (1) a magnitude AC1 of an alternating current (AC) component and a magnitude DC1 of a direct current (DC) component from a first pulse wave signal having a first wavelength, and (2) a magnitude AC2 of an alternating current (AC) component and a magnitude DC2 of a direct current (DC) component from a second pulse wave signal having a second wavelength. Further, the first feature value obtainer 710 may obtain a first feature value based on the obtained magnitudes of the AC component and the DC component.

For example, the first feature value obtainer 710 may divide a ratio (AC1/DC1) between the magnitude AC1 of the AC component and the magnitude DC1 of the DC component of the first pulse wave signal having the first wavelength by a ratio (AC2/DC2) between the magnitude AC2 of the AC component and the magnitude DC2 of the DC component of the second pulse wave signal having the second wavelength. In other words, the first feature value obtainer 710 may obtain, as the first feature value, a value obtained by ((AC1/DC1)÷(AC2/DC2)). The first wavelength may be a relatively longer wavelength than the second wavelength.

When the first feature value obtainer 710 obtains the first feature value for each channel, the optimal channel determiner 720 may determine an optimal channel based on a magnitude of the first feature value of each channel. For example, the optimal channel determiner 720 may determine, as the optimal channel, a channel having a highest first feature value or a predetermined number of channels in the order of a higher magnitude of the first value, starting from the highest first feature value.

The second feature value obtainer 730 may estimate a second feature value by using a pulse wave signal of the optimal channel determined by the optimal channel determiner 720. The second feature value obtainer 730 may generate an oscillogram by using at least one of the first pulse wave signal or the second pulse wave signal, e.g., a pulse wave signal having a relatively longer wavelength, of the determined optimal channel; and by using the generated oscillogram, the second feature value obtainer 730 may obtain, as the second feature value, a contact pressure value corresponding to an amplitude value at the maximum point MA of the pulse wave, and contact pressure values DP and SP at points to the left and right of the amplitude value at the maximum point MA of the pulse wave and having a preset ratio, e.g., 0.5 to 0.7, to the amplitude value at the maximum point MA, as described above. Alternatively, the second feature value obtainer 730 may generate the third oscillogram by generating the first oscillogram and the second oscillogram from the first pulse wave signal and the second pulse wave signal of the optimal channel, respectively, and may obtain the second feature value by using the generated third oscillogram.

In addition, the second feature value obtainer 730 may obtain the second feature value by analyzing the waveform of the pulse wave signal of the optimal channel. For example, the second feature value obtainer 730 may obtain, as the second feature value, a heart rate, a shape of a waveform, a time and/or an amplitude at a maximum point in a systolic phase of the pulse wave signal, a time and/or an amplitude at a minimum point of the pulse wave signal, a total or partial area of a waveform of the pulse wave signal, a duration of the pulse wave signal, an amplitude and/or a time of a waveform of a constituent pulse constituting the pulse wave signal, and the like.

The estimator 740 may estimate bio-information based on the first feature value, obtained by the first feature value obtainer 710, and/or the second feature value obtained by the second feature value obtainer 730. For example, the estimator 740 may estimate blood pressure using oscillometry, as described above. Alternatively, the estimator 740 may estimate bio-information by using a pre-defined bio-information estimation model. In this case, the bio-information estimation model may be expressed in the form of various linear or non-linear combination functions, such as addition, subtraction, division, multiplication, logarithmic value, regression equation, and the like, with no particular limitation.

Figure 9:
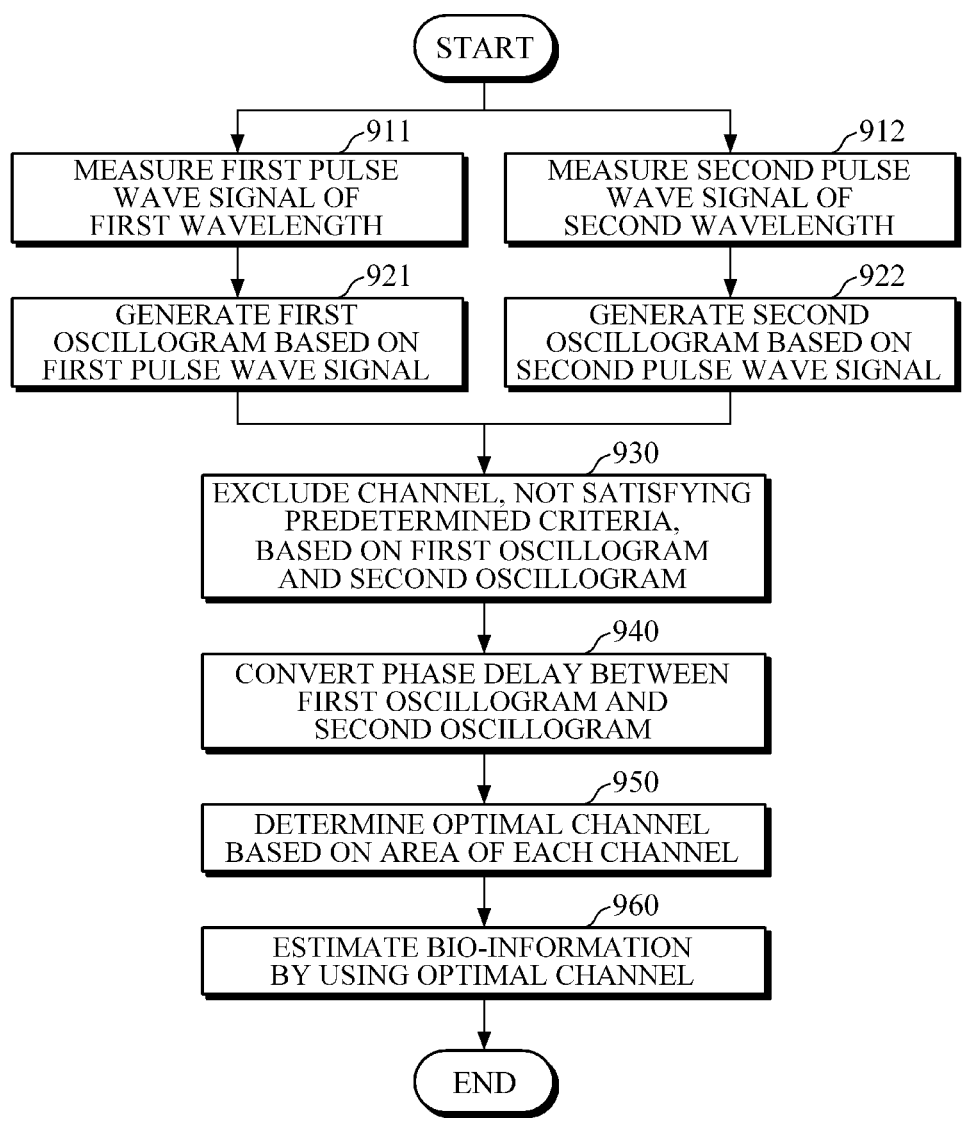
FIG. 9 is a flowchart illustrating a method of estimating bio-information according to an example embodiment.

FIG. 9 is a flowchart illustrating a method of estimating bio-information according to an example embodiment.

The method of FIG. 9 is an example of a method of estimating bio-information which is performed by any one of the apparatuses 100a and 100b for estimating bio-information according to the embodiments of FIGS. 1 and 2. Various embodiments thereof are described above in detail, and thus will be briefly described below.

First, the apparatuses 100a and 100b for estimating bio-information may measure, by each channel of a pulse wave sensor, a first pulse wave signal of a first wavelength in 911 and a second pulse wave signal of a second wavelength in 912. In this case, the first wavelength and the second wavelength may be different wavelengths. The apparatuses 100a and 100b for estimating bio-information may control the pulse wave sensor upon receiving a request for estimating bio-information from a user or if a predetermined criterion is satisfied. Various examples of the multi-channel pulse wave sensor for measuring pulse wave signals at multiple point of the object are described in detail above.

The apparatuses 100a and 100b for estimating bio-information may generate a first oscillogram based on the first pulse wave signal in 921, and may generate a second oscillogram based on the second pulse wave signal in 922.

Subsequently, the apparatuses 100a and 100b for estimating bio-information may exclude a channel, which does not satisfy a predetermined criterion, from a plurality of channels based on the first oscillogram and the second oscillogram which are generated for each channel in 930. For example, if a full width at half maximum (FWHM) of the pulse wave signal is greater than or equal to a predetermined threshold value, or if a statistical value such as a sum of residuals in the oscillogram is greater than or equal to a predetermined threshold value, the apparatuses 100a and 100b for estimating bio-information may exclude a corresponding channel. However, operation 930 may be omitted.

Next, the apparatuses 100a and 100b for estimating bio-information may convert a phase delay between the first oscillogram and the second oscillogram, which are generated for each channel, into an area in a Lissajous waveform in 940.

Then, the apparatuses 100a and 100b for estimating bio-information may determine an optimal channel based on the converted area of each channel in 950. For example, the apparatuses 100a and 100b for estimating bio-information may determine the optimal channel based on an area size, a slope of the Lissajous waveform, a shape of the area, an area ratio between the first region and the second region, and the like.

Subsequently, the apparatuses 100a and 100b for estimating bio-information may estimate bio-information by using the determined optimal channel in 960. For example, the apparatuses 100a and 100b for estimating bio-information may select the first oscillogram or the second oscillogram, or may generate a third oscillogram by subtracting the second oscillogram from the first oscillogram, and may estimate blood pressure by using the selected oscillogram or the generated third oscillogram.

Figure 10:
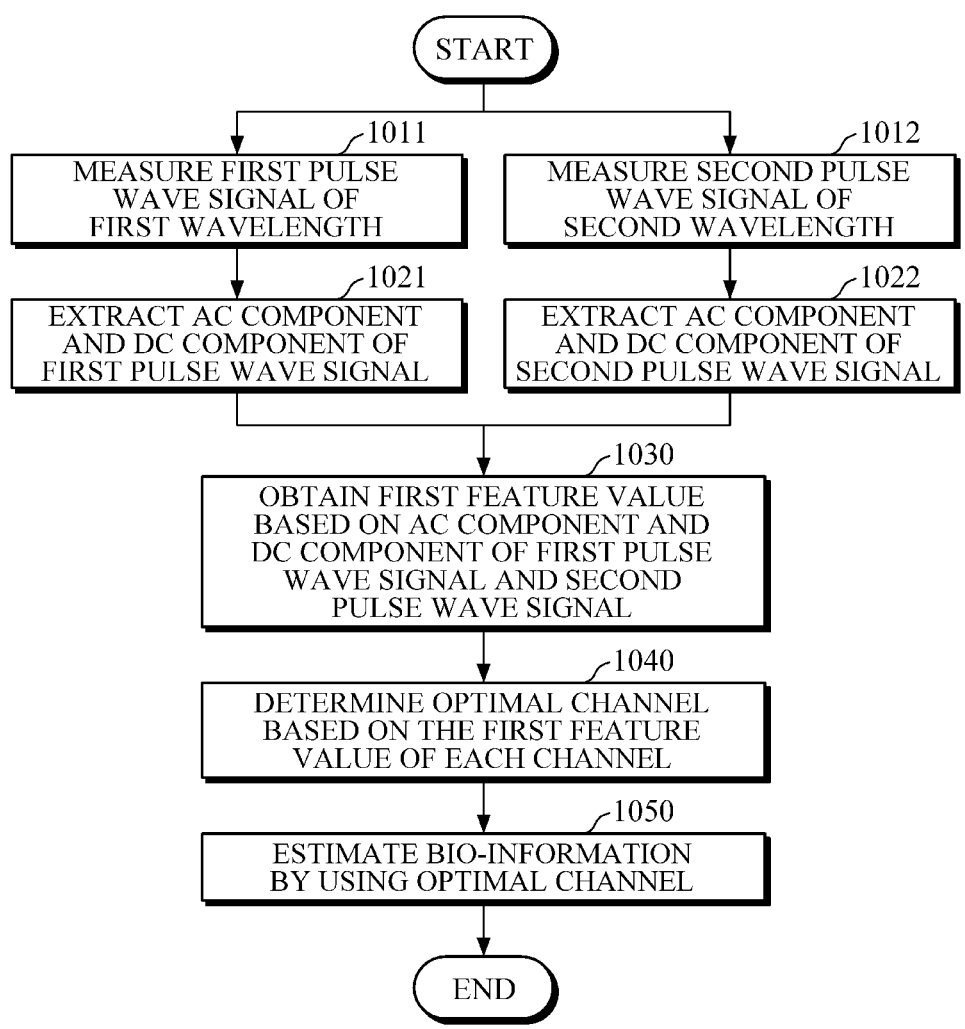
FIG. 10 is a flowchart illustrating a method of estimating bio-information according to an example embodiment.

FIG. 10 is a flowchart illustrating a method of estimating bio-information according to another embodiment.

The method of FIG. 10 is another example of a method of estimating bio-information which is performed by any one of the apparatuses 100a and 100b for estimating bio-information according to the embodiments of FIGS. 1 and 2. Various embodiments thereof are described above in detail, and thus will be briefly described below.

First, the apparatuses 100a and 100b for estimating bio-information may measure, by each channel of a pulse wave sensor, a first pulse wave signal of a first wavelength in 1011 and a second pulse wave signal of a second wavelength in 1012.

Then, the apparatuses 100a and 100b for estimating bio-information may extract an AC component and a DC component from the first pulse wave signal in 1021, and may extract an AC component and a DC component from the second pulse wave signal in 1022.

Subsequently, the apparatuses 100a and 100b for estimating bio-information may obtain a first feature value for each channel based on magnitudes of the AC component and the DC component of the first pulse wave signal and magnitudes of the AC component and the DC component of the second pulse wave signal in 1030. For example, the apparatuses 100a and 100b for estimating bio-information may obtain, as the first feature value for each channel, a value ((AC1/DC1)÷(AC2/DC2)), obtained by dividing a ratio (AC1/DC1) between the magnitude AC1 of the AC component and the magnitude DC1 of the DC component of the first pulse wave signal by a ratio (AC2/DC2) between the magnitude AC2 of the AC component and the magnitude DC2 of the DC component of the second pulse wave signal.

Next, the apparatuses 100a and 100b for estimating bio-information may determine an optimal channel based on the first feature value of each channel in 1040. For example, the apparatuses 100a and 100b for estimating bio-information may determine, as the optimal channel, one or a predetermined number of channels in the order of a higher magnitude of the first value of each channel, starting from the highest first feature value.

Then, the apparatuses 100a and 100b for estimating bio-information may estimate bio-information by using the determined optimal channel in 1050. For example, the apparatuses 100a and 100b for estimating bio-information may estimate bio-information using oscillometry based on the pulse wave signal of the optimal channel. Alternatively, the apparatuses 100a and 100b for estimating bio-information may obtain one or more second feature values by using the oscillogram of the optimal channel or by analyzing the waveform of the pulse wave signal. The apparatuses 100a and 100b for estimating bio-information may estimate bio-information by using a pre-defined bio-information estimation model based on the first feature value and/or the second feature value.

Figure 11:
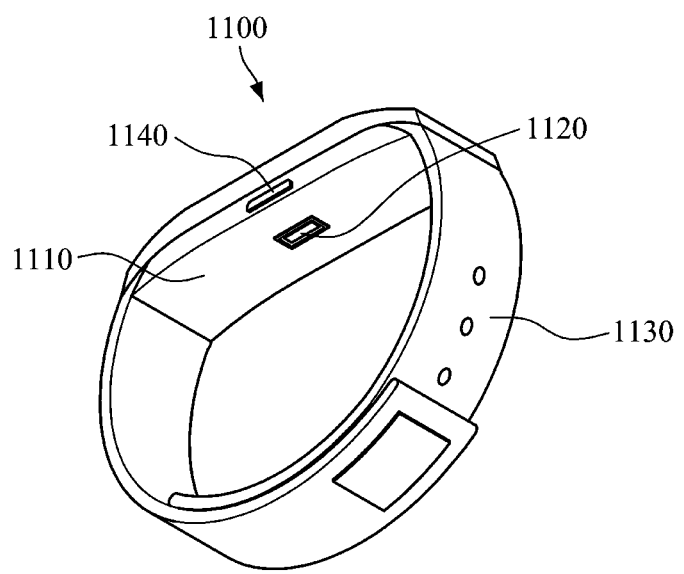
FIG. 11 is a diagram illustrating a wearable device according to an example embodiment.

FIG. 11 is a diagram illustrating a wearable device according to an example embodiment. The aforementioned embodiments of the apparatuses 100a and 100b for estimating bio-information may be mounted in the wearable device.

Referring to FIG. 11, the wearable device 1100 includes a main body 1110 and a strap 1130.

The strap 1130, which is connected to both ends of the main body 1110, may be flexible so as to be wrapped around a user's wrist. The strap 1130 may include a first strap and a second strap which are separated from each other. One ends of the first strap and the second strap are connected to the main body 1110, and the other ends thereof may be connected to each other via a connecting means. In this case, the connecting means may be formed as magnetic connection, Velcro connection, pin connection, and the like, but is not limited thereto. Further, the strap 1130 is not limited thereto, and may be integrally formed as a non-detachable band.

Air may be injected into the strap 1130, or the strap 1130 may be provided with an air bladder to have elasticity according to a change in pressure applied to the wrist, and may transmit the change in pressure of the wrist to the main body 1110.

A battery may be embedded in the main body 1110 or the strap 1130 to supply power to the wearable device 1100.

The main body 1110 may include a sensor part 1120 mounted thereon. The sensor part 1120 may include a pulse wave sensor for measuring pulse wave signals. The pulse wave sensor may include a light source that emits light onto skin of an object such as a wrist or a finger, a light receiver, such as a contact image sensor (CIS) optical sensor, a photodiode, etc., which detects light scattered or reflected from the wrist or the finger. The pulse wave sensor may have multiple channels for measuring pulse wave signals at multiple points of an object such as the wrist, the finger, etc., and each of the channels may include a light source and a light receiver, or may include a plurality of light sources configured to emit light of different wavelengths onto the object and/or a plurality of light receivers configured to detect light scattered or reflected from the object. The numbers of the light source and the light receiver included in each channel are not limited. In addition, the sensor part 1120 may further include a force sensor configured to measure a contact force between the object such as the wrist or finger and the sensor part 1120.

A processor may be mounted in the main body 1110. The processor may be electrically connected to modules mounted in the wearable device 1100. As described above, when the sensor part 1120 obtains pulse wave signals for each channel, the processor may determine an optimal channel and may estimate bio-information by using a pulse wave signal of the determined optimal channel. A detailed description thereof will be omitted.

Further, the main body 1110 may include a storage which stores reference information for estimating blood pressure and performing various functions of the wearable device 1100, and information processed by various modules thereof.

In addition, the main body 1110 may include a manipulator 1140 which is provided on one side surface of the main body 1110, and receives a user's control command and transmits the received control command to the processor. The manipulator 1140 may have a power button to input a command to turn on/off the wearable device 1100.

Further, a display for outputting information to a user may be mounted on a front surface of the main body 1110. The display may have a touch screen to receive a touch input. The display may receive a user's touch input and transmit the touch input to the processor, and may display processing results of the processor.

Moreover, the main body 1110 may include a communication interface for communication with an external device. The communication interface may transmit a blood pressure estimation result to the external device, e.g., a user's smartphone.

Figure 12:
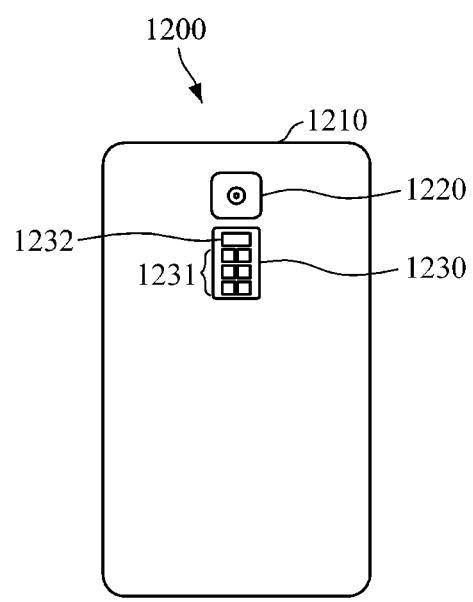
FIG. 12 is a diagram illustrating a smart device according to an example embodiment.

FIG. 12 is a diagram illustrating a smart device according to an example embodiment. The smart device may include a smartphone, a tablet PC, and the like. The smart device may include functions of the aforementioned apparatuses 100a and 100b for estimating bio-information.

Referring to FIG. 12, the smart device 1200 includes a main body 1210 and a pulse wave sensor 1230 mounted on one surface of the main body 1210. For example, the pulse wave sensor 1230 may include one or more light sources 1232 disposed at a predetermined position(s) thereof. The one or more light sources 1232 may emit light of different wavelengths. In addition, a plurality of light receivers 1231 may be disposed at positions spaced apart from the light sources 1232 by a predetermined distance. However, this is merely an example, and the pulse wave sensor 1230 may have various shapes and configurations. Further, a force sensor for measuring a contact force of a finger may be mounted in the main body 1210 at a lower end of the pulse wave sensor 1230.

Moreover, a display may be mounted on a front surface of the main body 1210. The display may visually output a blood pressure estimation result, a health condition evaluation result, and the like. The display may include a touch screen, and may receive information input through the touch screen and transmit the information to a processor.

The main body 1210 may include an image sensor 1220 as illustrated in FIG. 12. The image sensor 1220 may capture various images, and may acquire, for example, a fingerprint image of a finger being in contact with the pulse wave sensor 1230. In addition, when an image sensor based on the CIS technology is mounted in the light receivers 1231 of the pulse wave sensor 1230, the image sensor 1220 may be omitted.

As described above, the processor may determine an optimal channel based on the pulse wave signals measured by the pulse wave sensor 1230 and may estimate bio-information based on the determined optimal channel. A detailed description thereof will be omitted.

The disclosure may be implemented by using a computer-readable code written on a computer-readable recording medium. The computer-readable recording medium may be any type of recording device in which data is stored in a computer-readable manner.

Examples of the computer-readable recording medium include a ROM, a RAM, a CD-ROM, a magnetic tape, a floppy disc, an optical data storage, and a carrier wave (e.g., data transmission through the Internet). The computer-readable recording medium may be distributed over a plurality of computer systems connected to a network so that a computer-readable code is written thereto and executed therefrom in a decentralized manner. Functional programs, codes, and code segments needed for implementing the disclosure may be readily deduced by programmers of ordinary skill in the art to which the disclosure pertains.

At least one of the components, elements, modules or units described herein may be embodied as various numbers of hardware, software and/or firmware structures that execute respective functions described above, according to an example embodiment. For example, at least one of these components, elements or units may use a direct circuit structure, such as a memory, a processor, a logic circuit, a look-up table, etc. that may execute the respective functions through controls of one or more microprocessors or other control apparatuses. Also, at least one of these components, elements or units may be specifically embodied by a module, a program, or a part of code, which contains one or more executable instructions for performing specified logic functions, and executed by one or more microprocessors or other control apparatuses. Also, at least one of these components, elements or units may further include or implemented by a processor such as a central processing unit (CPU) that performs the respective functions, a microprocessor, or the like. Two or more of these components, elements or units may be combined into one single component, element or unit which performs all operations or functions of the combined two or more components, elements of units. Also, at least part of functions of at least one of these components, elements or units may be performed by another of these components, element or units. Further, although a bus is not illustrated in the above block diagrams, communication between the components, elements or units may be performed through the bus. Functional aspects of the above example embodiments may be implemented in algorithms that execute on one or more processors. Furthermore, the components, elements or units represented by a block or processing operations may employ any number of related art techniques for electronics configuration, signal processing and/or control, data processing and the like.

The disclosure has been described herein with regard to example embodiments. However, it will be obvious to those skilled in the art that various modifications may be made without departing from the gist of the disclosure. Therefore,

What is claimed is:

1. An apparatus for estimating bio-information without using a cuff, the apparatus comprising:
a storage configured to store a light source driving condition, a condition for selecting an optimal channel, and a condition for excluding a channel;
a pulse wave sensor including a plurality of channels, each channel comprising at least one light source and at least one light receiver, each channel of the plurality of channels being configured to measure, from an object, a first pulse wave signal of a first wavelength and a second pulse wave signal of a second wavelength that is different from the first wavelength;
at least one of a force sensor or a pressure sensor configured to measure a contact pressure exerted between the object and the pulse wave sensor; and
a processor configured to:
obtain the light source driving condition from the storage, and drive the at least one light source of each channel according to the light source driving condition;
for each channel of the plurality of channels, by plotting a peak-to-peak amplitude at each measurement time against the contact pressure exerted between the object and the pulse wave sensor at a corresponding time, generate a first oscillogram representing a change of an amplitude of the first pulse wave signal with respect to a change in the contact pressure, and generate a second oscillogram representing a change of an amplitude of the second pulse wave signal with respect to the change in the contact pressure;
obtain the condition for excluding a channel from the storage, and exclude a channel, of which the first oscillogram and the second oscillogram do not satisfy a predetermined criterion;
for remaining channels among the plurality of channels, after exclusion, convert a phase delay between the first oscillogram and the second oscillogram into an area; and
obtain the condition for selecting the optimal channel from the storage, select a channel among the plurality of channels based on the area of each channel according to the condition for selecting the optimal channel, and estimate bio-information based on the selected channel,
wherein the processor is further configured to guide a user in real time on the contact pressure exerted between the object and the pulse wave sensor based on the contact pressure measured in real time by the at least one of the force sensor or the pressure sensor while the first pulse wave signal and the second pulse wave signal are measured.

2. The apparatus of claim 1, wherein, in the pulse wave sensor,
the at least one light source is configured to emit light of the first wavelength and light of the second wavelength onto the object, and
the at least one light receiver is configured to detect the light of the first wavelength and the light of the second wavelength, which is scattered or reflected from the object.

3. The apparatus of claim 2, wherein the at least one light receiver comprises at least one of a photodiode array or a complementary metal-oxide semiconductor (CMOS) image sensor.

4. The apparatus of claim 1, wherein the area of each channel is in a Lissajous waveform.

5. The apparatus of claim 4, wherein the processor is further configured to select the channel based on at least one of a size of the area, a slope of the Lissajous waveform, a shape of the area, or a ratio between a first region and a second region, the first region and the second region being obtained by dividing the area of each channel.

6. The apparatus of claim 1, wherein the processor is further configured to:
generate, for each channel of the plurality of channels, a third oscillogram based on subtracting the second oscillogram from the first oscillogram, and
in selecting the channel, exclude a channel based on at least one of a full width at half maximum (FWHM) in the third oscillogram, a full width at a point corresponding to a predetermined ratio between a baseline point and a maximum point of the third oscillogram, or a statistical value of residuals between a pulse wave before curve fitting of the third oscillogram and a pulse wave after the curve fitting of the third oscillogram.

7. The apparatus of claim 1, wherein the processor is further configured to estimate the bio-information by using the first oscillogram of the selected channel, the second oscillogram of the selected channel, or a third oscillogram generated by subtracting the second oscillogram of the selected channel from the first oscillogram of the selected channel.

8. The apparatus of claim 1, wherein the processor is further configured to estimate first bio-information by using the first oscillogram, estimate second bio-information by using the second oscillogram, and obtain final bio-information based on at least one of the first bio-information or the second bio-information.

9. The apparatus of claim 1, wherein the processor is further configured to select two or more channels among the plurality of channels based on the area of each channel of the plurality of channels, estimate bio-information values of respective selected two or more channels, and obtain final bio-information by using at least one of the estimated bio-information values of the respective selected two or more channels.

10. The apparatus of claim 1, wherein the bio-information comprises at least one of a blood pressure, a vascular age, an arterial stiffness, an aortic pressure waveform, a vascular compliance, a stress index, a fatigue level, a skin age, or a skin elasticity.

11. A method of estimating bio-information without using a cuff, the method comprising:
storing, in a storage, a light source driving condition, a condition for selecting an optimal channel, and a condition for excluding a channel;
by using a pulse wave sensor having a plurality of channels, each channel comprising at least one light source and at least one light receiver, measuring, from an object for each channel of the plurality of channels, a first pulse wave signal of a first wavelength and a second pulse wave signal of a second wavelength that is different from the first wavelength;
by using at least one of a force sensor or a pressure sensor, measuring a contact pressure exerted between the object and the pulse wave sensor;

guiding a user in real time on the contact pressure exerted between the object and the pulse wave sensor based on the contact pressure measured in real time by the at least one of the force sensor or the pressure sensor while the first pulse wave signal and the second pulse wave signal are measured;

obtaining the light source driving condition from the storage, and driving the at least one light source of each channel according to the light source driving condition;

by plotting a peak-to-peak amplitude at each measurement time against the contact pressure exerted between the object and the pulse wave sensor at a corresponding time, generating a first oscillogram representing a change of an amplitude of the first pulse wave signal with respect to a change in the contact pressure, and generating a second oscillogram representing a change of an amplitude of the second pulse wave signal with respect to the change in the contact pressure;

obtaining the condition for excluding a channel from the storage, and excluding a channel, of which the first oscillogram and the second oscillogram do not satisfy a predetermined criterion;

for remaining channels among the plurality of channels, after exclusion, converting, for each channel of the plurality of channels, a phase delay between the first oscillogram and the second oscillogram into an area;

obtaining the condition for selecting the optimal channel from the storage, and selecting a channel among the plurality of channels based on the area of each channel according to the condition for selecting the optimal channel; and estimating bio-information based on the selected channel.

12. The method of claim 11, wherein the area of each channel is in a Lissajous waveform.

13. The method of claim 12, wherein the selecting comprises selecting the channel based on at least one of a size of the area, a slope of the Lissajous waveform, a shape of the area, or a ratio between a first region and a second region, the first region and the second region being obtained by dividing the area of each channel.

14. The method of claim 11, further comprising:

generating, for each channel of the plurality of channels, a third oscillogram by subtracting the second oscillogram from the first oscillogram, wherein, in the selecting the channel, a channel is excluded based on at least one of a full width at half maximum (FWHM) in the third oscillogram, a full width at a point corresponding to a predetermined ratio between a baseline point and a maximum point of the third oscillogram, or a statistical value of residuals between a pulse wave before curve fitting of the third oscillogram and a pulse wave after the curve fitting of the third oscillogram.

15. The method of claim 11, wherein the estimating comprises estimating the bio-information by using the first oscillogram of the selected channel, the second oscillogram of the selected channel, or a third oscillogram generated by subtracting the second oscillogram of the selected channel from the first oscillogram of the selected channel.

16. The method of claim 11, wherein the estimating comprises estimating first bio-information by using the first oscillogram of the selected channel, estimating second bio-information by using the second oscillogram of the selected channel, and obtaining final bio-information based on at least one of the first bio-information or the second bio-information.

17. The method of claim 11, wherein the estimating comprises selecting two or more channels among the plurality of channels based on the area of each channel, estimating bio-information values of respective selected two or more channels, and obtaining final bio-information by using at least one of the estimated bio-information values of the respective selected two or more channels.

\* \* \* \* \*